(12) United States Patent
Sato et al.

(10) Patent No.: US 11,872,320 B2
(45) Date of Patent: Jan. 16, 2024

(54) METHOD FOR TREATING OSTEOARTHRITIS

(71) Applicant: HISAMITSU PHARMACEUTICAL CO., INC., Tosu (JP)

(72) Inventors: Hiroyuki Sato, Tokyo (JP); Hirochika Takano, Tokyo (JP)

(73) Assignee: HISAMITSU PHARMACEUTICAL CO., INC., Tosu (JP)

(*) Notice: Subject to any disclaimer, the term of this patent is extended or adjusted under 35 U.S.C. 154(b) by 0 days.

(21) Appl. No.: 17/184,797

(22) Filed: Feb. 25, 2021

(65) Prior Publication Data

US 2022/0265567 A1 Aug. 25, 2022

(51) Int. Cl.
- A61K 47/12 (2006.01)
- A61K 31/196 (2006.01)
- A61K 9/70 (2006.01)
- A61K 9/00 (2006.01)

(52) U.S. Cl.
CPC .......... *A61K 9/7053* (2013.01); *A61K 9/0014* (2013.01); *A61K 9/7076* (2013.01); *A61K 31/196* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 4,421,737 A | 12/1983 | Ito et al. | |
| 4,695,465 A | 9/1987 | Kigasawa et al. | |
| 4,738,848 A | 4/1988 | Yoshida et al. | |
| 5,208,035 A | 5/1993 | Okuyama et al. | |
| 5,776,484 A | 7/1998 | Sasaki et al. | |
| 5,869,087 A | 2/1999 | Hirano et al. | |
| 5,914,322 A | 6/1999 | Falk et al. | |
| 5,916,587 A | 6/1999 | Min et al. | |
| 5,945,125 A | 8/1999 | Kim | |
| 6,086,911 A | 7/2000 | Godbey | |
| 6,262,121 B1 | 7/2001 | Kawaji et al. | |
| 6,451,339 B2 | 9/2002 | Patel et al. | |
| 6,616,941 B1 | 9/2003 | Seo | |
| 9,308,187 B2 | 4/2016 | Hatanaka et al. | |
| 2002/0106401 A1 | 8/2002 | Hori et al. | |
| 2003/0149383 A1 | 8/2003 | Ikeura et al. | |
| 2003/0175331 A1 | 9/2003 | Sasaki et al. | |
| 2004/0092696 A1 | 5/2004 | Vedula et al. | |
| 2004/0146548 A1 | 7/2004 | Takada et al. | |
| 2005/0129748 A1 | 6/2005 | Takada et al. | |
| 2006/0093656 A1 | 5/2006 | Muta et al. | |
| 2006/0200063 A1 | 9/2006 | Munro et al. | |
| 2006/0234581 A1 | 10/2006 | Saito et al. | |
| 2007/0148218 A1 | 6/2007 | Gordon | |
| 2012/0071808 A1 | 3/2012 | Sato et al. | |
| 2012/0215186 A1 | 8/2012 | Kydonieus et al. | |
| 2012/0283671 A1 | 11/2012 | Shibata et al. | |
| 2013/0211351 A1 | 8/2013 | Fuhrherr et al. | |
| 2015/0202171 A1 | 7/2015 | Hatanaka et al. | |
| 2015/0224063 A1 | 8/2015 | Ogino et al. | |
| 2015/0297507 A1 | 10/2015 | Grenier et al. | |
| 2017/0348246 A1 | 12/2017 | Tohara et al. | |
| 2019/0350874 A1 | 11/2019 | Tanaka et al. | |
| 2019/0374481 A1* | 12/2019 | Nardi .................... A61K 47/20 |

FOREIGN PATENT DOCUMENTS

| | | |
|---|---|---|
| CA | 1144070 A1 | 4/1983 |
| CA | 2200068 A1 | 3/1996 |
| CA | 2380128 A1 | 6/2001 |
| CN | 1111987 A | 11/1995 |
| CN | 1489996 A | 4/2004 |
| CN | 1628634 A | 6/2005 |
| CN | 1705472 A | 12/2005 |
| CN | 101442993 A | 5/2009 |
| CN | 101530401 A | 9/2009 |
| CN | 101932329 A | 12/2010 |
| CN | 102448449 A | 5/2012 |
| CN | 103893156 A | 7/2014 |
| CN | 104379139 A | 2/2015 |
| CN | 106619580 A | 5/2017 |
| CN | 106999343 A | 8/2017 |
| CN | 110114064 A | 8/2019 |
| EP | 0524582 A1 | 1/1993 |
| EP | 0997144 A1 | 5/2000 |
| EP | 1477164 A1 | 11/2004 |
| EP | 2196197 A1 | 6/2010 |

(Continued)

OTHER PUBLICATIONS

International Search Report dated Apr. 26, 2022 corresponding to application No. PCT/JP2022/007229.
"Diclonac Na PAP 70mg Rakool"; 2014.
"Clinical Effect of Diclofenac Sodium Tape Formulation (Voltaren Tape) on Pain Disease"; Therapeutic Research; vol. 26, No. 12; 2005.
Matsunaga, et al. "Clinical Experience of Diclofenac Sodium Cream on Osteoarthritis of the Knee and Rheumatoid Arthritis"; vol. 11, No. 8; Aug. 1983.
"A Comparative Study of Diclofenac Sodium Percutaneous Agent (TP318) and its Base Preparation in Treating Osteoarthrosis of the Knee Conclusion"; 2000.

(Continued)

*Primary Examiner* — Alton N Pryor

(74) *Attorney, Agent, or Firm* — Nath, Goldberg & Meyer; Joshua B. Goldberg

(57) ABSTRACT

Disclosed is a method for treating osteoarthritis comprising a step of administering a patch to a patient. The patch comprises a backing layer and an adhesive layer laminated on the backing layer, the adhesive layer comprises an adhesive base, diclofenac sodium, dimethyl sulfoxide, and an organic acid, and a content of the organic acid is 6 mass % to 8 mass % with respect to a total mass of the adhesive layer. The patch is applied to an affected part once a day, and a dose of diclofenac sodium per administration is 70 mg to 150 mg.

50 Claims, No Drawings

(56) References Cited

FOREIGN PATENT DOCUMENTS

| | | |
|---|---|---|
| EP | 2370067 B1 | 11/2013 |
| EP | 2865378 A1 | 4/2015 |
| GB | 2045618 A | 11/1980 |
| GB | 2073588 A | 10/1981 |
| JP | 61233077 A1 | 10/1986 |
| JP | S61-280426 A | 12/1986 |
| JP | S62-181226 A | 8/1987 |
| JP | 63246326 A | 10/1988 |
| JP | 4103528 A | 4/1992 |
| JP | 5155762 A | 6/1993 |
| JP | 5201879 A | 8/1993 |
| JP | 6024969 A | 2/1994 |
| JP | H6219940 A | 8/1994 |
| JP | 8026985 A | 1/1996 |
| JP | H8-500365 A | 1/1996 |
| JP | 9208460 A | 8/1997 |
| JP | 9315957 A | 12/1997 |
| JP | 10182450 A | 7/1998 |
| JP | 10218793 A | 8/1998 |
| JP | 2816765 B2 | 10/1998 |
| JP | 11035458 A | 2/1999 |
| JP | 11255644 A | 9/1999 |
| JP | 11322590 A | 11/1999 |
| JP | H11-322595 A | 11/1999 |
| JP | 2001058961 A1 | 3/2001 |
| JP | 2001-233769 A | 8/2001 |
| JP | 2002-020274 A | 1/2002 |
| JP | 2002-193793 A | 7/2002 |
| JP | 2002-226366 A | 8/2002 |
| JP | 2002-338462 A | 11/2002 |
| JP | 2003-063955 A | 3/2003 |
| JP | 2003-319967 A | 11/2003 |
| JP | 2006-206454 A | 8/2006 |
| JP | 2006288887 A | 10/2006 |
| JP | 200715963 A | 1/2007 |
| JP | 2007-511605 A | 5/2007 |
| JP | 2008508954 A | 3/2008 |
| JP | 2011162514 A | 8/2011 |
| JP | 2001-302502 A | 10/2011 |
| JP | 5075378 B2 | 8/2012 |
| JP | 2013-535438 A | 9/2013 |
| JP | 2014148582 A1 | 9/2014 |
| JP | 2015-522049 A | 8/2015 |
| JP | 2016-222631 A | 12/2016 |
| JP | 2019-107220 A | 7/2019 |
| JP | 6744511 B1 * | 8/2020 |
| KR | 0191062 B1 | 6/1999 |
| KR | 20000068581 | 11/2000 |
| KR | 2002-0012978 A | 2/2002 |
| KR | 1020150023758 A | 3/2015 |
| TW | 201406411 A | 2/2014 |
| TW | 201828931 A | 8/2018 |
| TW | 202139988 A | 11/2021 |
| TW | 202139989 A | 11/2021 |
| TW | 202139990 A * | 11/2021 |
| TW | 202139990 A | 11/2021 |
| WO | 9608245 A1 | 3/1996 |
| WO | 9954422 A1 | 10/1999 |
| WO | 0178690 A1 | 10/2001 |
| WO | WO-0178690 A1 * | 10/2001 ........... A61K 31/192 |
| WO | 2004058232 A1 | 7/2004 |
| WO | 2006017807 A2 | 2/2006 |
| WO | 2009096315 A1 | 8/2009 |
| WO | 2010137699 A1 | 12/2010 |
| WO | 2011/083787 A1 | 7/2011 |
| WO | 2011136330 A1 | 11/2011 |
| WO | 2012/009262 A2 | 1/2012 |
| WO | 2012022837 A1 | 2/2012 |
| WO | 2013191128 A1 | 12/2013 |
| WO | 2014134073 A1 | 9/2014 |
| WO | 2014148582 A1 | 9/2014 |
| WO | 2014181840 A1 | 11/2014 |
| WO | 2015105101 A1 | 7/2015 |
| WO | 2018070370 A1 | 4/2018 |
| WO | 2018124089 A1 | 7/2018 |
| WO | 2018141661 A1 | 8/2018 |
| WO | 2018141662 A1 | 8/2018 |
| WO | WO-2018141662 A1 * | 8/2018 ........... A61K 31/167 |

OTHER PUBLICATIONS

Rakool Pharmaceutical Marketing Co., Ltd., "Package insert for- "Rakool" Diclofenac Na PAP 70mg, 140mg, 280mg", 2006.
"Office Action dated Feb. 18, 2015 in Japanese Patent Application No. 2014-521452 (with partial English language translation)".
"International Search Report dated Sep. 3, 2013 in PCT/JP2013/066574".
"International Preliminary Report on Patentability and Written Opinion dated Dec. 31, 2014 in PCT/JP2013/066574".
"Philip Fuller, et al., "Diclofenac sodium topical solution with dimethyl sulfoxide, a viable alternative to oral nonsteroidal antiinflammatories in osteoarthritis: review of current evidence",, Journal of Multidisciplinary Healthcare, Abstract, vol. 4, 2011,pp. 223-231".
"Rajesh Dubey, et al., "Ketorolac Tromethamine Transdermal Gel: Development, In Vitro and In Vivo Evaluation", J. Pain Palliat, Care Pharmacother, vol. 23, No. 1, 2009, pp. 26-34".
"Office Action in Korean Application No. 10-2015-7000960 dated Feb. 8, 2019".
"Taiwanese Office Action dated Nov. 21, 2016 in corr. Taiwanese Patent Application No. 102122030".
"Hewitt, P.G., et al., "In Vitro Cutaneous Disposition of a Topical Diclofenac Lotion in Human Skin: Effect of a Multi-Dose Regimen", Pharmaceutical Research, vol. 15, No. 7, Jul. 1998, pp. 988-992".
"Extended European Search Report dated Feb. 3, 2016 in Application No. 13807634.4".
Canadian Office Action dated Oct. 22, 2010 correspoding to application No. 2519195.
Chinese Office Action dated Oct. 13, 2006 corresponding to application No. 200480007150.X.
"Adhesive compn. for low polar plastic resins-comprises an alky(meth)acrylate copolymer, and tackifier comprising rosin and hydrogenerated petroleum resin", Jan. 27, 1995, xp002216523, two pages.
Supplementary European Search Report under Article 153(7) EPC, dated Aug. 16, 2010, five pages.
Chinese Notice of Rejection dated May 22, 2007 corresponding to application No. 200480007150.X.
Office Action dated Dec. 27, 2010 corresponding to European application No. 04721660.1.
Office Action dated Nov. 5, 2010 corresponding to Korean application No. 10-2005-7017273.
Machine Translation of 2001-302502A.
Non-Final Office Action dated Dec. 21, 2022 corresponding U.S. Appl. No. 17/244,552.
Office Action dated Jun. 10, 2023 corresponding to CN Patent Application No. 202180013224.4.
Taiwanese Office Action dated Mar. 3, 2021 corresponding to application No. 106146207.
Japanese Office Action dated Feb. 2, 2021 corresponding to application No. P2018-559525.
Korean Office Action dated Oct. 16, 2020 corresponding to application No. 10-2019-7017157.
Extended European Search Report dated Jun. 29, 2020 corresponding to application No. 178873667-1109.
Office Action dated Dec. 17, 2019 corresponding to Taiwanese application No. 106146207.
International Preliminary Report on Patenability dated Jul. 11, 2019 corresponding to application No. PCT/JP2017/046697.
Taiwanese Office Action dated Aug. 22, 2022 corresponding to application No. 110104894.
Taiwanese Office Action dated Aug. 16, 2022 corresponding to application No. 110104895.
Office Action dated Aug. 17, 2022 corresponding to U.S. Appl. No. 17/184,797.

(56) References Cited

OTHER PUBLICATIONS

Chinese Office Action dated Mar. 2, 2022 corresponding to application No. 201780080620.2.
Taiwanese Office Action dated Feb. 25, 2022 corresponding to application No. 109106150.
International Preliminary Report on Patentability dated Sep. 10, 2021 corresponding to application No. PCT/JP2020/007182.
International Search Report dated Apr. 14, 2020 corresponding to application No. PCT/JP2020/007182.
Simon, LS et al. , "Efficacy and safety of topical diclofenac containing dimethyl sulfoxide (DMSO) compared with DMSO those of topical placebo, DMSO vehicle and oral diclofenac for knee osteoarthritis: Pain", vol. 143, Issue 3, https://doi.org/10.1016/j.pain.2009.03.008, Jun. 2009, p. 238-p. 245.
Office Action dated Apr. 25, 2023 corresponding to BR Patent Application No. BR112021016517-7.
International Preliminary Report on Patentability dated Aug. 11, 2022 corresponding to application No. PCT/JP2021/004740.
International Preliminary Report on Patentability dated Aug. 11, 2022 corresponding to application No. PCT/JP2021/004741.
International Preliminary Report on Patentability dated Aug. 11, 2022corresponding to application No. PCT/JP2021/004819.
Office Action dated Jul. 29, 2023 corresponding to CN Patent Application No. 202080016834.5.

* cited by examiner

METHOD FOR TREATING OSTEOARTHRITIS

TECHNICAL FIELD

The present invention relates to a method for treating osteoarthritis.

BACKGROUND

A method for administering a transdermal preparation comprising diclofenac has been proposed as a method for treating osteoarthritis (US 20150297507 A1). A topical preparation comprising diclofenac sodium includes, for example, a patch comprising diclofenac sodium, dimethyl sulfoxide, and citric acid (US 20150202171 A1).

Treatment for osteoarthritis which is likely to occur due to disorders of bones, muscles, joints, nerves, and the like is expected to become more and more important in modern society in the future. For this reason, it is desirable to develop a patch which has excellent drug release ability and skin permeability and is effective and safe for human osteoarthritis.

SUMMARY

The present inventors have studied in detail a composition of a patch for treating osteoarthritis comprising a high concentration of diclofenac sodium, and an administration method of the patch, and as a result, they have found that a patch which is effective and safe, thus leading to realization of the present invention.

The method for treating osteoarthritis of the present invention comprises: a step of administering a patch to a patient, wherein the patch comprises a backing layer and an adhesive layer laminated on the backing layer, wherein the adhesive layer comprises an adhesive base, diclofenac sodium, dimethyl sulfoxide, and an organic acid, wherein a content of the organic acid is 6 mass % to 8 mass % with respect to a total mass of the adhesive layer, wherein the patch is applied to an affected part once a day, and wherein a dose of diclofenac sodium per administration is 70 mg to 150 mg.

DETAILED DESCRIPTION

A method for treating osteoarthritis of the present invention comprises a step of administering a patch to a patient.

The patch comprises a backing layer and an adhesive layer laminated on the backing layer. The adhesive layer is usually laminated on one surface of the backing layer, and a peelable film is laminated on the other surface of the adhesive layer as necessary.

The adhesive layer is a site which is adhered to the skin during application of the patch, and comprises an adhesive base, diclofenac sodium, dimethyl sulfoxide, and an organic acid.

Diclofenac sodium is a nonsteroidal anti-inflammatory drug and is an active ingredient for treating osteoarthritis. The content of diclofenac sodium is preferably 1 mass % to 10 mass % or 3 mass % to 7 mass % with respect to the total mass of the adhesive layer.

The adhesive base may be at least one selected from a rubber-based adhesive base, an acrylic-based adhesive base, and a silicone-based adhesive base. The rubber-based adhesive base includes, for example, polyisoprene, polyisobutylene (PIB), polybutadiene, a styrene-butadiene-styrene block copolymer, a styrene-isoprene-styrene (SIS) block copolymer, styrene-butadiene rubber, styrene-isoprene rubber, or a combination thereof. Among these, a SIS block copolymer, PIB, or a combination thereof is preferable and a mixture of an SIS block copolymer and PIB is more preferable from the viewpoint of enhancing skin permeability of diclofenac sodium as well as further enhancing adhesiveness of the patch. The acrylic-based adhesive base includes, for example, an adhesive obtained by polymerizing or copolymerizing at least one of (meth)acrylic monomers such as (meth)acrylic acid, 2-ethylhexyl (meth)acrylate, methyl (meth)acrylate, butyl (meth)acrylate, and hydroxyethyl (meth)acrylate. The silicone-based adhesive base includes, for example, a silicone rubber such as polydimethylsiloxane, polymethylvinylsiloxane, or polymethylphenylsiloxane as a main component.

The content of an adhesive base in the case of a rubber-based adhesive base is preferably 10 mass % to 70 mass %, 20 mass % to 50 mass %, 23 mass % to 40 mass %, or 25 mass % to 30 mass % with respect to the total mass of the adhesive layer from the viewpoint of the adhesiveness of the patch. In a case where a mixture of an SIS block copolymer and PIB is used as a rubber-based adhesive base, the mass ratio thereof is preferably 4:1 to 1:4, 3:1 to 1:1, or 3:1 to 2:1. The content of an adhesive base in the case of an acrylic-based adhesive base or a silicone-based adhesive base is preferably 50 mass % to 90 mass % with respect to the total mass of the adhesive layer.

Dimethyl sulfoxide (DMSO) enhances solubility of diclofenac sodium and improves skin permeability of diclofenac sodium. The content of DMSO is preferably 1 mass % to 20 mass %, 2 mass % to 10 mass %, 3 mass % to 10 mass %, or 5 mass % to 9 mass % with respect to the total mass of the adhesive layer.

The ratio of diclofenac sodium and DMSO is preferably 1:0.3 to 1:4, 1:0.4 to 1:3, 1:0.6 to 1:3, or 1:0.72 to 1:3 from the viewpoint of improving the skin permeability of diclofenac sodium and the viewpoint of preventing precipitation of crystals of diclofenac sodium.

An organic acid promotes transdermal absorption of diclofenac sodium and/or prevents crystals of diclofenac sodium from precipitating over time. Examples of organic acids include aliphatic carboxylic acids such as aliphatic monocarboxylic acids (such as formic acid, acetic acid, propionic acid, butyric acid, isobutyrate, valeric acid, caproic acid, enanthic acid, caprylic acid, nonanoic acid, capric acid, lauric acid, oleic acid, linoleic acid, linolenic acid, isostearic acid, sorbic acid, and pyruvic acid), aliphatic dicarboxylic acids (such as oxalic acid, malonic acid, succinic acid, glutaric acid, adipic acid, sebacic acid, maleic acid, fumaric acid, and oxaloacetic acid), and aliphatic tricarboxylic acids (such as aconitic acid and propanetricarboxylic acid), hydroxy acids (such as glycolic acid, lactic acid, tartronic acid, glyceric acid, hydroxybutyric acid, malic acid, tartaric acid, citric acid, isocitric acid, saccharic acid, gluconic acid, glucuronic acid, ascorbic acid, and erythorbic acid), aromatic carboxylic acids (such as benzoic acid, gallic acid, salicylic acid, acetylsalicylic acid, and phthalic acid), and other organic acids (such as mesylic acid and besylic acid). These organic acids may be used alone or in a combination of two or more thereof. Among these organic acids, oleic acid, citric acid, mesylic acid, or a combination thereof is preferable and a combination of oleic acid and citric acid is more preferable from the viewpoints of promoting transdermal absorption of diclofenac sodium and preventing crystals of diclofenac sodium from precipitating over time. The content of an organic acid is 6 mass % to 8 mass % with respect to the total mass of an adhesive layer from the viewpoint of effectiveness of treatment of osteoarthritis. In a case where an organic acid is a combination of oleic acid and citric acid, it is preferable that the content of oleic acid be 4 mass % to 6 mass % with respect to the total mass of the adhesive layer and the content of citric acid with respect to the total mass of the adhesive layer be 2 mass % to 4 mass %.

The adhesive layer may further comprise other additives such as a tackifier, a plasticizer, a solubilizer, a stabilizer, and a filler.

Examples of tackifiers include rosin, rosin derivatives such as glycerin ester of rosin, hydrogenated rosin, hydrogenated rosin glycerin ester, and pentaerythritol ester of rosin, alicyclic saturated hydrocarbon resins such as Alcon P100 and Alcon P115 (which are the names of products manufactured by Arakawa Chemical Industries, Ltd.), aliphatic hydrocarbon resins such as Quintone B170 (the name of a product manufactured by Zeon Corporation), terpene resins such as YS resin PX1150N and Clearon P-125 (which are the names of products manufactured by YASUHARA CHEMICAL CO., LTD.), and maleic acid resin. Among these, hydrogenated rosin glycerin esters, alicyclic saturated hydrocarbon resins, aliphatic hydrocarbon resins, or terpene resins are preferable and alicyclic saturated hydrocarbon resins are more preferable. Two or more kinds of these tackifier resins may be combined. The presence of a tackifier resin can improve the adhesiveness of the adhesive layer and stably maintain other properties.

It is preferable that the content of a tackifier resin be, for example, 5 mass % to 60 mass %, 10 mass % to 50 mass %, 30 mass % to 45 mass %, or 35 mass % to 40 mass % based on the total mass of the adhesive layer. A combination of an alicyclic saturated hydrocarbon resin and a hydrogenated rosin glycerin ester is more preferable as a tackifier. The mass ratio of an alicyclic saturated hydrocarbon resin and a hydrogenated rosin glycerin ester is preferably 4:1 to 1:4, 4:1 to 2:3, or 3:1 to 2:1.

Examples of plasticizers include petroleum oils such as paraffinic process oils, naphthenic process oils, and aromatic process oils; squalane; squalene; vegetable oils such as olive oil, camellia oil, castor oil, tall oil, and peanut oil; silicon oils; dibasic acid esters such as dibutylphthalate and dioctylphthalate; liquid rubber such as polybutene and liquid isoprene rubber; liquid fatty acid esters such as isopropyl myristate, hexyl laurate, diethyl sebacate, and diisopropyl sebacate; diethylene glycol; polyethylene glycol; glycol salicylate; propylene glycol; dipropylene glycol; triacetin; triethyl citrate; and crotamiton. Among these, liquid paraffin, liquid polybutene, isopropyl myristate, diethyl sebacate, and hexyl laurate are preferable, liquid polybutene, isopropyl myristate, and liquid paraffin are more preferable, and liquid paraffin is particularly preferable. Two or more kinds of these plasticizers may be combined. The content of a plasticizer is preferably 7 mass % to 70 mass %, 8 mass % to 40 mass %, 10 mass % to 20 mass %, or 12 mass % to 15 mass % with respect to the total mass of the adhesive layer.

Examples of solubilizers include liquid fatty acid esters (such as isopropyl myristate, hexyl laurate, diethyl sebacate, and diisopropyl sebacate), diethylene glycol, triethylene glycol, polyethylene glycol, propylene glycol, dipropylene glycol, triacetin, triethyl citrate, and crotamiton. Among these, diethylene glycol, triethylene glycol, polyethylene glycol, propylene glycol, and dipropylene glycol are preferable, and polyethylene glycol is more preferable. In a case where a solubilizer is polyethylene glycol, the number average molecular weight of polyethylene glycol may be 200 to 20,000, preferably 400 to 6,000, and more preferably 1,000 to 6,000. Two or more kinds of these solubilizers may be combined. The content of a solubilizer is preferably 0.1 mass % to 10 mass % or 0.5 mass % to 5 mass % based on the total mass of the adhesive layer.

Examples of stabilizers include fatty acid metal salts (such as zinc undecylenate, zinc stearate, magnesium stearate, calcium stearate, aluminum stearate, sodium stearate, zinc palmitate, zinc myristate, magnesium myristate, zinc laurate, and sodium laurate), antioxidants (such as tocopherol derivatives, ascorbic acid derivatives, erythorbic acid derivatives, nordihydroguaiaretic acid, gallic acid derivatives, dibutylhydroxytoluene (BHT), butylhydroxyanisole, and 2-mercaptobenzimidazole), and ultraviolet absorbents (such as imidazole derivatives, benzotriazole derivatives, p-aminobenzoic acid derivatives, anthranilic acid derivatives, salicylic acid derivatives, cinnamic acid derivatives, benzophenone derivatives, coumaric acid derivatives, and camphor derivatives). Two or more kinds of these stabilizers may be combined. Among these stabilizers, aliphatic metal salts are preferable, at least one component selected from the group consisting of zinc stearate and magnesium stearate is more preferable, and a combination of zinc stearate and magnesium stearate is particularly preferable. The content of a stabilizer is preferably 0 mass % to 5 mass % or 0 mass % to 2 mass % based on the total mass of the adhesive layer. The presence of a stabilizer in the adhesive layer can improve the stability of diclofenac sodium.

Examples of fillers include metal oxides (such as zinc oxide and titanium oxide), metal salts (such as calcium carbonate, magnesium carbonate, and zinc stearate), silicic acid compounds (such as kaolin, talc, bentonite, AEROSIL, hydrous silica, aluminum silicate, magnesium silicate, and magnesium aluminometasilicate), and metal hydroxides (such as aluminum hydroxide). Two or more kinds of these fillers may be combined. The content of a filler is preferably 0 mass % to 10 mass % or 0 mass % to 5 mass % based on the total mass of the adhesive layer.

The adhesive layer may be a single layer consisting of one composition, or may be a plurality of laminated layers having different compositions. A mass of an adhesive mass of the whole adhesive layer is preferably 10 g/m$^2$ to 1,000 g/m$^2$, 30 g/m$^2$ to 300 g/m$^2$, 150 g/m$^2$ to 250 g/m$^2$, or 190 g/m$^2$ to 240 g/m$^2$ from the viewpoint of making the patch appropriately adhere to the skin. In addition, when the specific gravity of the adhesive layer is 1, the thickness of the entire adhesive layer is preferably 10 μm to 1,000 μm, 30 μm to 300 μm, 150 μm to 250 μm, or 190 μm to 240 μm.

Next, a backing layer will be described. The backing layer supports an adhesive layer. The backing layer is preferably a single-layer body or a laminated body of a cloth-like fiber (woven fabric, non-woven fabric, or knitted fabric) or a non-porous or porous film (sheet). The material of a backing layer is preferably one or more materials selected from polyesters (such as polyethylene terephthalate (PET), polyethylene isophthalate, polypropylene terephthalate polypropylene isophthalate, polybutylene terephthalate, and polyethylene naphthalate), polyolefins (polymers or copolymers of vinyl monomers such as ethylene, propylene, vinyl acetate, or acrylonitrile), polyamides (nylon or silk), polyurethanes (PU), or cellulose (such as cotton or hemp). Cloth (woven fabric, non-woven fabric, or knitted fabric) may be coated with a rubber composition. The rubber composition comprises a rubber adhesive. The rubber adhesive includes, for example, polyisoprene, PIB, polybutadiene, a styrene-butadiene-styrene block copolymer, a SIS block copolymer, styrene-butadiene rubber, styrene-isoprene rubber, or a combination thereof. The rubber composition may comprise a tackifier. The tackifier includes, for example, an alicyclic saturated hydrocarbon resin, a hydrogenated rosin ester, a terpene resin, or a combination thereof. In addition, the rubber composition may further comprise additives such as a plasticizer or a filler. The thickness of the backing layer is, for example, 0.1 mm to 2 mm. The basis weight of the backing layer is, for example, 30 g/m² to 200 g/m². In the present specification, the thickness and the basis weight of the backing layer are measured in accordance with the JIS L 1913:2010 standard.

The moisture permeability of the backing layer is preferably 1,000 g/m²·24 hours or more. When a backing layer having such high moisture permeability is used, DMSO gradually volatilizes from the patch applied to the skin. Therefore, the adhesiveness of the patch is improved and the patch is unlikely to peel off even when it is applied for a long period of time. The upper limit value of the moisture permeability may be 20,000 g/m²·24 hours. When the moisture permeability of the backing layer is within such a range, DMSO more easily volatilizes from the adhesive layer, and therefore the backing layer is more effective for improving the adhesiveness of the patch. The moisture permeability of the backing layer is moisture permeability at 40° C. which is defined in accordance with the JIS Z0208:1976 standard (moisture permeability test method (cup method)) of the moisture-proof packaging material).

In a case where the backing layer has a cloth shape, the 50% modulus (JIS L 1018:1999) of the backing layer in either the longitudinal direction (material flow direction) or the lateral direction (material width direction) is also preferably 1 N/50 mm to 12 N/50 mm. In a case where the 50% modulus is less than or equal to 12 N/50 mm, the amount of stress applied to the patch due to expansion and contraction of the skin is smaller, and therefore the adhesion to the skin is favorable.

In a case where the backing layer is a film, the material thereof is preferably one such as a polyurethane having high moisture permeability (high DMSO permeability). Since a film made of a polyurethane has excellent stretchability, it is preferable from the viewpoint of enhancing adhesion of the patch to the skin and stretch followability of the patch.

The backing layer is preferably, for example, a film or non-woven fabric made of a polyurethane, knitted fabric made of polyethylene terephthalate, polyester cloth coated with a rubber composition, or a combination thereof. More specifically, the backing layer is preferably a laminated body of a film made of polyurethane and non-woven fabric made of a polyurethane fiber, non-woven fabric made of a PET fiber, or polyester cloth coated with a rubber composition.

Next, a peelable film (a release film or a release liner) will be described. A peelable film may be one which can cover an adhesive layer before use of the patch and can peel off and be removed when in use, and specific examples thereof include films of polyesters such as polyethylene terephthalate and polyethylene naphthalate, polyolefins such as polyethylene and polypropylene, polyvinyl chloride, and polyvinylidene chloride, laminated films of fine paper and polyolefin, and films of nylon and aluminum. As these peelable films, ones subjected to surface coating (peeling treatment) with a release agent such as silicone or polytetrafluoroethylene are preferably used from the viewpoint that these peelable films can easily peel off from an adhesive layer.

In order to secure sufficient adhesive strength and a sufficient skin permeation amount of diclofenac sodium, the application area of the patch is preferably 30 cm² to 300 cm², 50 cm² to 150 cm², or 70 cm² to 140 cm².

The patch can be produced, for example, through the following method, but the present invention is not limited thereto and well-known methods can be used. First, components constituting an adhesive layer are mixed with each other at predetermined proportions to give a homogeneous dissolved material. Then, the dissolved material is spread on a peelable film or a backing layer to a predetermined thickness to form an adhesive layer. Subsequently, a backing layer is adhered to the adhesive layer or the peelable film so that the adhesive layer is sandwiched between the peelable film and the backing layer. Finally, the patch can be obtained by cutting the laminated body into a predetermined shape. In this case, the peelable film is removed at the time of applying the patch. In addition, similarly, the dissolved material may be spread on a backing layer to a predetermined thickness to form an adhesive layer, and then the backing layer may be adhered to a peelable film.

The patch is applied to an affected part (such as a knee, a groin, an elbow, or a shoulder) of a human adult once a day and is replaced every day (about 24 hours). The dose of diclofenac sodium per administration is 70 mg to 150 mg. The dose is the content of diclofenac sodium in the patch to be applied. The dose may be a content of diclofenac sodium in one patch, or may be a total content of diclofenac sodium in a plurality of patches. For example, in a case where one patch comprising 70 mg to 150 mg of diclofenac sodium per sheet is applied, the dose thereof is 70 mg to 150 mg. For example, in a case where one or two patches comprising 75 mg of diclofenac sodium per sheet is applied, the dose thereof is 75 mg or 150 mg. For example, in a case where two or three patches comprising 50 mg of diclofenac sodium per sheet is applied, the dose thereof is 100 mg or 150 mg.

The patch is effective for treating osteoarthritis. More specifically, it is effective in alleviating pain of osteoarthritis. Of osteoarthritis, the patch is particularly effective for knee osteoarthritis. In a case where the patch is used for treating osteoarthritis, the patch is preferably alternately applied to inner and outer sides of a knee every day. Such administration can avoid skin irritation, increase the local concentration of diclofenac sodium in the knee joint, and increase the therapeutic effect of knee osteoarthritis.

In a case where a single dose of the patch is administered to a human adult, it is preferable that the maximum plasma concentration ($C_{max}$) of diclofenac is 19 ng/mL to 23 ng/mL, that the time ($t_{max}$) required to reach the maximum plasma concentration is 6 hours to 18 hours, that the area under plasma drug concentration-time curve of diclofenac ($AUC_{0-t}$) from the time of administration to a final time point of concentration measurement is 300 ng·h/mL to 400 ng·h/mL, that the area under drug plasma concentration-time curve ($AUC_{0-inf}$) of diclofenac when extrapolated from the time of administration to infinite time is 300 ng·h/mL to 400 ng·h/mL, that the half-life ($t_{1/2}$) of the plasma concentration of diclofenac is 6 hours to 8 hours, that the amount (apparent dose) of diclofenac released is 13 mg to 16 mg, and that the release rate (% drug released) of diclofenac is 8.6% to 10.7%. A patch showing such pharmacokinetic parameters has excellent safety and effectiveness in treatment of osteoarthritis.

In a case where administration of the patch once a day is repeated to a human adult to reach a steady state, it is preferable that the maximum plasma concentration ($C^{ss}_{max}$) of diclofenac is 30 ng/mL to 65 ng/mL, that the time ($t^{ss}_{max}$) required to reach the maximum plasma concentration ($C^{ss}_{max}$) is 3 hours to 6 hours, that the area under drug plasma concentration-time curve ($AUC^{ss}_{0-\tau}$) of diclofenac at an administration interval is 400 ng·h/mL to 700 ng·h/mL, that the half-life ($t^{ss}_{1/2}$) of the plasma concentration of diclofenac is 1 hours to 5 hours, that the amount (apparent dose) of diclofenac released is 14 mg to 21 mg, and that the release rate (% drug released) of diclofenac is 9.3% to 14%. A patch showing such pharmacokinetic parameters has excellent safety and effectiveness in treatment of osteoarthritis.

Other preferred embodiments of the present invention are as follows.

[1] A patch for treating osteoarthritis, comprising a backing layer and an adhesive layer laminated on the backing layer, wherein the adhesive layer comprises an adhesive base, diclofenac sodium, dimethyl sulfoxide, and an organic acid, wherein a content of the organic acid is 6 mass % to 8 mass % with respect to a total mass of the adhesive layer, and wherein the patch is used to be applied to an affected part once a day and so that a dose of diclofenac sodium per administration is 70 mg to 150 mg.

[2] The patch of [1], wherein an area of the patch is 70 cm$^2$ to 140 cm$^2$.

[3] The patch of [1] or [2], wherein a mass of an adhesive mass of the patch is 190 g/m$^2$ to 240 g/m$^2$.

[4] The patch of any one of [1] to [3], wherein osteoarthritis is knee osteoarthritis.

[5] The patch of [4], wherein the patch is alternately applied to inner and outer sides of a knee every day.

[6] The patch of any one of [1] to [5], wherein the patch shows a maximum plasma concentration of diclofenac of 19 to 23 ng/mL during a single dose and a time required to reach the maximum plasma concentration of 6 to 18 hours.

[7] The patch of any one of [1] to [6], wherein the patch shows an area under plasma drug concentration-time curve of diclofenac of 300 ng·h/mL to 400 ng·h/mL from the time of a single dose to a final time point of concentration measurement.

[8] The patch of any one of [1] to [7], wherein the patch shows an area under plasma drug concentration-time curve of diclofenac of 300 ng·h/mL to 400 ng·h/mL when extrapolated from the time of a single dose to infinite time.

[9] The patch of any one of [1] to [8], wherein the patch shows a half-life of the plasma concentration of diclofenac of 6 hours to 8 hours during a single dose.

[10] The patch of any one of [1] to [9], wherein the patch shows an amount of diclofenac released of 13 mg to 16 mg during a single dose and a release rate of diclofenac of 8.6% to 10.7%.

[11] The patch of any one of [1] to [10], wherein the patch shows a maximum plasma concentration of diclofenac of 30 ng/mL to 65 ng/mL when administration once a day is repeated to reach a steady state and a time required to reach the maximum plasma concentration of 3 to 6 hours.

[12] The patch of any one of [1] to [11], wherein the patch shows an area under plasma drug concentration-time curve of diclofenac of 400 ng·h/mL to 700 ng·h/mL at an administration interval when administration once a day is repeated to reach a steady state.

[13] The patch of any one of [1] to [12], wherein the patch shows a half-life of the plasma concentration of diclofenac of 1 hour to 5 hours when administration once a day is repeated to reach a steady state.

[14] The patch of any one of [1] to [13], wherein the patch shows an amount of diclofenac released of 14 mg to 21 mg when administration once a day is repeated to reach a steady state and a release rate of diclofenac of 9.3% to 14%.

[15] The patch of any one of [1] to [14], wherein the patch comprises a styrene-isoprene-styrene block copolymer and polyisobutylene as the adhesive base.

[16] The patch of any one of [1] to [15], wherein the patch comprises an alicyclic saturated hydrocarbon resin and a hydrogenated rosin glycerin ester in the adhesive layer.

[17] The patch of any one of [1] to [16], wherein the patch comprises liquid paraffin in the adhesive layer.

[18] The patch of any one of [1] to [17], wherein the patch comprises 3 mass % to 7 mass % of diclofenac sodium with respect to a total mass of the adhesive layer.

[19] The patch of any one of [1] to [18], wherein the patch comprises oleic acid and citric acid as the organic acids.

[20] The patch of any one of [1] to [19], wherein the patch comprises 4 mass % to 6 mass % of oleic acid and 2 mass % to 4 mass % of citric acid with respect to a total mass of the adhesive layer.

[21] A patch for use in a method for treating osteoarthritis, the patch comprising a backing layer and an adhesive layer laminated on the backing layer, wherein the adhesive layer comprises an adhesive base, diclofenac sodium, dimethyl sulfoxide, and an organic acid, wherein a content of the organic acid is 6 mass % to 8 mass % with respect to a total mass of the adhesive layer, and wherein the patch is used to be applied to an affected part once a day and so that a dose of diclofenac sodium per administration is 70 mg to 150 mg.

[22] The patch for use of [21], wherein an area of the patch is 70 cm$^2$ to 140 cm$^2$.

[23] The patch for use of [21] or [22], wherein a mass of an adhesive mass of the patch is 190 g/m$^2$ to 240 g/m$^2$.

[24] The patch for use of any one of [21] to [23], wherein osteoarthritis is knee osteoarthritis.

[25] The patch for use of [24], wherein the patch is alternately applied to inner and outer sides of a knee every day.

[26] The patch for use of any one of [21] to [25], wherein the patch shows a maximum plasma concentration of diclofenac of 19 to 23 ng/mL during a single dose and a time required to reach the maximum plasma concentration of 6 to 18 hours.

[27] The patch for use of any one of [21] to [26], wherein the patch shows an area under plasma drug concentration-time curve of diclofenac of 300 ng·h/mL to 400 ng·h/mL from the time of a single dose to a final time point of concentration measurement.

[28] The patch for use of any one of [21] to [27], wherein the patch shows an area under plasma drug concentration-time curve of diclofenac of 300 ng·h/mL to 400 ng·h/mL when extrapolated from the time of a single dose to infinite time.

[29] The patch for use of any one of [21] to [28], wherein the patch shows a half-life of the plasma concentration of diclofenac of 6 hours to 8 hours during a single dose.

[30] The patch for use of any one of [21] to [29], wherein the patch shows an amount of diclofenac released of 13 mg to 16 mg during a single dose and a release rate of diclofenac of 8.6% to 10.7%.

[31] The patch for use of any one of [21] to [30], wherein the patch shows a maximum plasma concentration of diclofenac of 30 ng/mL to 65 ng/mL when administration once a day is repeated to reach a steady state and a time required to reach the maximum plasma concentration of 3 to 6 hours.

[32] The patch for use of any one of [21] to [31], wherein the patch shows an area under plasma drug concentration-time curve of diclofenac of 400 ng·h/mL to 700 ng·h/mL at an administration interval when administration once a day is repeated to reach a steady state.

[33] The patch for use of any one of [21] to [32], wherein the patch shows a half-life of the plasma concentration of diclofenac of 1 hour to 5 hours when administration once a day is repeated to reach a steady state.

[34] The patch for use of any one of [21] to [33], wherein the patch shows an amount of diclofenac released of 14 mg to 21 mg when administration once a day is repeated to reach a steady state and a release rate of diclofenac of 9.3% to 14%.

[35] The patch for use of any one of [21] to [34], wherein the patch comprises a styrene-isoprene-styrene block copolymer and polyisobutylene as the adhesive base.

[36] The patch for use of any one of [21] to [35], wherein the patch comprises an alicyclic saturated hydrocarbon resin and a hydrogenated rosin glycerin ester in the adhesive layer.

[37] The patch for use of any one of [21] to [36], wherein the patch comprises liquid paraffin in the adhesive layer.

[38] The patch for use of any one of [21] to [37], wherein the patch comprises 3 mass % to 7 mass % of diclofenac sodium with respect to a total mass of the adhesive layer.

[39] The patch for use of any one of [21] to [38], wherein the patch comprises oleic acid and citric acid as the organic acids.

[40] The patch for use of any one of [21] to [39], wherein the patch comprises 4 mass % to 6 mass % of oleic acid and 2 mass % to 4 mass % of citric acid with respect to a total mass of the adhesive layer.

EXAMPLES

1. Preparation of Patch Comprising Diclofenac Sodium

A patch comprising diclofenac sodium was prepared by the following method. Ingredients (ingredients shown in Table 1) of an adhesive layer were homogenously mixed with each other and were spread on a release liner (a PET liner subjected to release treatment) so that the mass of the adhesive mass was 214 g/m². A backing layer was laminated on the spread adhesive layer, the laminated body was cut into a size of 100 cm² to give a patch (in which the content of diclofenac sodium per unit area was 10.7 g/m² and one patch comprises 107 mg of diclofenac sodium).

TABLE 1

| Ingredients | Example 1 | Comparative Example 1 |
|---|---|---|
| Diclofenac sodium | 5 | 5 |
| Rubber adhesive base (SIS/polyisobutylene) | 27 (19/8) | 21 (15/6) |
| Tackifier resin (Alicyclic saturated hydrocarbon resin/Hydrogenated rosin glycerin ester = 27/10) | 37 | 37 |
| Liquid paraffin | 12.9 | 24.4 |
| Oleic acid | 5 | 3 |
| Anhydrous citric acid | 2.1 | 1.8 |
| Dimethyl sulfoxide | 7 | 7 |
| Zinc stearate | 0.4 | 0 |
| Magnesium stearate | 3 | 0 |
| Synthetic aluminum silicate | 0 | 0.2 |
| Others | 0.6 | 0.6 |
| Total % | 100 | 100 |

2. Preparation of Placebo Patch

A placebo patch comprising no diclofenac sodium was prepared by the same method as that described above. Ingredients of an adhesive layer of the placebo patch are shown in Table 2.

TABLE 2

| Components | Placebo |
|---|---|
| Diclofenac sodium | 0 |
| Rubber adhesive base (SIS/polyisobutylene = 19/8) | 22.4 |
| Tackifier resin (Alicyclic saturated hydrocarbon resin/Hydrogenated rosin glycerin ester = 27/10) | 38.9 |
| Liquid paraffin | 25.4 |
| Oleic acid | 3.2 |
| Anhydrous citric acid | 1.9 |
| Dimethyl sulfoxide | 7.4 |
| Synthetic aluminum silicate | 0.2 |
| Others | 0.6 |
| Total % | 100 |

3. Effectiveness Test for Patch

Screening of Subject

Of patients with knee osteoarthritis, subjects to be participated in this test were screened using the Numerical Rating Scale (which is a gradual scale which indicates the current degree of pain where 0 is no pain and 10 is the maximum imaginable pain in 11 stages from 0 to 10; hereinafter, referred to as the "NRS scale").

Application of Patch to Subjects

The subjects determined to be eligible through the screening were assigned to any of the groups of the patch of Example 1, the patch of Comparative Example 1, and the placebo patch, and the patches were alternately applied to inner and outer sides of a knee every day for 4 consecutive weeks. It was prohibited to change the dose during the application period.

Evaluation Criteria for Effectiveness

The change in Western Ontario and McMaster Universities Osteoarthritis Index (WOMAC) LK3.10A pain score between the start (base line) of application and the 4th week of application was measured. The WOMAC LK3.10A pain score is widely used as a measure specific to osteoarthritis. The following five items were evaluated on a 5-point scale <scale from 0 to 4>, and the lower the numerical value, the better the result <0=not difficult, 4=significantly difficult>.

1. Walking
2. Stair climbing
3. Nocturnal
4. Rest
5. Weight bearing

Results

As is apparent from the results shown in Table 3, the patch-administered group (N=69) of Example 1 was statistically significantly improved (pain alleviation) compared to the placebo patch-administered group (N=143).

TABLE 3

| | Change on 4th week from base line | |
|---|---|---|
| | Example 1 (N = 69) | Comparative Example 1 (N = 71) |
| Difference (standard error) from placebo of least square means | −1.49 (0.583) | −0.62 (0.577) |
| 95% Confidence interval | (−2.64, −0.34) | (−1.75, 0.51) |
| P Value | 0.0110 | 0.2835 |

4. Pharmacokinetic Test of Patch
Preparation of Patch Comprising Diclofenac Sodium Patches (in which the content of diclofenac sodium per unit area was 10.7 g/m² and one patch comprises 150 mg of diclofenac sodium) of Example 2 and Comparative Example 2 were obtained with the same compositions as Example 1 and Comparative Example 1 of the 1 except that the area of a patch was cut into a size of 140 cm².

Application of Patch to Subjects

The patch of Example 2 and the patch of Comparative Example 2 or the patch of Comparative Example 2 and the patch of Example 2 were applied to the knees of 18 healthy subjects in this order, and the pharmacokinetics of a single dose and a plurality of doses of diclofenac sodium was evaluated.

Results

Results of the single dose and the plurality of doses are respectively shown in Tables 4 and 5. The numerical values in the tables represent average values (% coefficient of variation), while $T_{max}$ and $t^{ss}_{max}$ represent the median (minimum value-maximum value).

TABLE 4

|  | Example 2 | Comparative Example 2 |
|---|---|---|
| $C_{max}$ (ng/mL) | 20.9 (73) | 18.1 (68) |
| $t_{max}$ (hr) | 18 (6-18) | 12 (3-18) |
| $AUC_{0-t}$ (ng·h/mL) | 343 (75) | 272 (70) |
| $AUC_{0-inf}$ (ng·h/mL) | 347 (74) | 274 (69) |
| $t_{1/2}$ (hr) | 6.57 (41) | 5.7 (62) |
| Apparent Dose (mg) | 14.2 (33) | 12.5 (37) |
| % Drug released (%) | 9.3 (33) | 8.0 (37) |

TABLE 5

|  | Example 2 | Comparative Example 2 |
|---|---|---|
| $C^{ss}_{max}$ (ng/mL) | 49.0 (49) | 25.1 (85) |
| $C^{ss}_{min}$ (ng/mL) | 10.2 (40) | 6.99 (50) |
| $t^{ss}_{max}$ (hr) | 3 (3-6) | 3 (3-18) |
| $AUC^{ss}_{0-tau}$ (ng·h/mL) | 558 (47) | 319 (76) |
| $t^{ss}_{1/2}$ (hr) | 2.99 (26) | 3.41 (29) |
| Apparent Dose (mg) | 17.2 (27) | 12.4 (48) |
| % Drug released (%) | 11.2 (27) | 7.9 (48) |

What is claimed is:

1. A method for treating osteoarthritis, the method comprising: a step of administering a patch to a patient,
   wherein the patch comprises a backing layer and an adhesive layer laminated on the backing layer,
   wherein the adhesive layer comprises an adhesive base, diclofenac sodium, dimethyl sulfoxide, and one or more organic acids,
   wherein a content of the organic acid is 6 mass % to 8 mass % with respect to a total mass of the adhesive layer,
   wherein the patch is applied to an affected part of the patient once a day,
   wherein a dose of diclofenac sodium per administration is 70 mg to 150 mg, and
   wherein the patch comprises a styrene-isoprene-styrene block copolymer and polyisobutylene as the adhesive base, and wherein the patch shows an amount of diclofenac released of 13 mg to 16 mg during a single dose and a release rate of diclofenac of 8.6% to 10.7%.

2. The method of claim 1, wherein an area of the patch is 70 cm² to 140 cm².

3. The method of claim 1, wherein a mass of an adhesive mass of the patch is 190 g/m² to 240 g/m².

4. The method of claim 1, wherein the osteoarthritis is knee osteoarthritis.

5. The method of claim 4, wherein the patch is alternately applied to inner and outer sides of a knee every day.

6. The method of claim 1, wherein the patch shows a maximum plasma concentration of diclofenac of 19 to 23 ng/mL during a single dose and a time required to reach the maximum plasma concentration of 6 to 18 hours.

7. The method of claim 1, wherein the patch shows an area under plasma drug concentration-time curve of diclofenac of 300 ng·h/mL to 400 ng·h/mL from the time of a single dose to a final time point of concentration measurement.

8. The method of claim 1, wherein the patch shows an area under plasma drug concentration-time curve of diclofenac of 300 ng·h/mL to 400 ng·h/mL when extrapolated from the time of a single dose to infinite time.

9. The method of claim 1, wherein the patch shows a half-life of plasma concentration of diclofenac of 6 hours to 8 hours during a single dose.

10. The method of claim 1, wherein the patch shows an amount of diclofenac released of 13 mg to 16 mg during a single dose and a release rate of diclofenac of 8.6% to 10.7%.

11. The method of claim 1, wherein the patch shows a maximum plasma concentration of diclofenac of 30 ng/mL to 65 ng/mL when administration once a day is repeated to reach a steady state and a time required to reach the maximum plasma concentration of 3 to 6 hours.

12. The method of claim 1, wherein the patch shows an area under plasma drug concentration-time curve of diclofenac of 400 ng·h/mL to 700 ng·h/mL at an administration interval when administration once a day is repeated to reach a steady state.

13. The method of claim 1, wherein the patch shows a half-life of the plasma concentration of diclofenac of 1 hour to 5 hours when administration once a day is repeated to reach a steady state.

14. The method of claim 1, wherein the patch shows an amount of diclofenac released of 14 mg to 21 mg when administration once a day is repeated to reach a steady state and a release rate of diclofenac of 9.3% to 14%.

15. The method of claim 1, wherein the patch comprises 3 mass % to 7 mass % of diclofenac sodium with respect to a total mass of the adhesive layer.

16. The method of claim 1, wherein the patch comprises oleic acid and citric acid as the organic acids.

17. The method of claim 16, wherein the patch comprises 4 mass % to 6 mass % of the oleic acid and 2 mass % to 4 mass % of the citric acid with respect to a total mass of the adhesive layer.

18. A method for treating osteoarthritis, the method comprising: a step of administering a patch to a patient,
   wherein the patch comprises a backing layer and an adhesive layer laminated on the backing layer,
   wherein the adhesive layer comprises an adhesive base, diclofenac sodium, dimethyl sulfoxide, and one or more organic acids,
   wherein a content of the organic acid is 6 mass % to 8 mass % with respect to a total mass of the adhesive layer,
   wherein the patch is applied to an affected part of the patient once a day, wherein a dose of diclofenac sodium per administration is 70 mg to 150 mg, and wherein the patch comprises an alicyclic saturated hydrocarbon resin and a hydrogenated rosin glycerin ester in the adhesive layer, and wherein the patch shows an amount of diclofenac released of 13 mg to 16 mg during a single dose and a release rate of diclofenac of 8.6% to 10.7%.

19. The method of claim 18, wherein an area of the patch is 70 cm$^2$ to 140 cm$^2$.

20. The method of claim 18, wherein a mass of an adhesive mass of the patch is 190 g/m$^2$ to 240 g/m$^2$.

21. The method of claim 18, wherein the osteoarthritis is knee osteoarthritis.

22. The method of claim 21, wherein the patch is alternately applied to inner and outer sides of a knee every day.

23. The method of claim 18, wherein the patch shows a maximum plasma concentration of diclofenac of 19 to 23 ng/mL during a single dose and a time required to reach the maximum plasma concentration of 6 to 18 hours.

24. The method of claim 18, wherein the patch shows an area under plasma drug concentration-time curve of diclofenac of 300 ng·h/mL to 400 ng·h/mL from the time of a single dose to a final time point of concentration measurement.

25. The method of claim 18, wherein the patch shows an area under plasma drug concentration-time curve of diclofenac of 300 ng·h/mL to 400 ng·h/mL when extrapolated from the time of a single dose to infinite time.

26. The method of claim 18, wherein the patch shows a half-life of plasma concentration of diclofenac of 6 hours to 8 hours during a single dose.

27. The method of claim 18, wherein the patch shows a maximum plasma concentration of diclofenac of 30 ng/mL to 65 ng/mL when administration once a day is repeated to reach a steady state and a time required to reach the maximum plasma concentration of 3 to 6 hours.

28. The method of claim 18, wherein the patch shows an area under plasma drug concentration-time curve of diclofenac of 400 ng·h/mL to 700 ng·h/mL at an administration interval when administration once a day is repeated to reach a steady state.

29. The method of claim 18, wherein the patch shows a half-life of the plasma concentration of diclofenac of 1 hour to 5 hours when administration once a day is repeated to reach a steady state.

30. The method of claim 18, wherein the patch shows an amount of diclofenac released of 14 mg to 21 mg when administration once a day is repeated to reach a steady state and a release rate of diclofenac of 9.3% to 14%.

31. The method of claim 18, wherein the patch comprises 3 mass % to 7 mass % of diclofenac sodium with respect to a total mass of the adhesive layer.

32. The method of claim 18, wherein the patch comprises oleic acid and citric acid as the organic acids.

33. The method of claim 32, wherein the patch comprises 4 mass % to 6 mass % of the oleic acid and 2 mass % to 4 mass % of the citric acid with respect to a total mass of the adhesive layer.

34. A method for treating osteoarthritis, the method comprising: a step of administering a patch to a patient,
wherein the patch comprises a backing layer and an adhesive layer laminated on the backing layer,
wherein the adhesive layer comprises an adhesive base, diclofenac sodium, dimethyl sulfoxide, and one or more organic acids,
wherein a content of the organic acid is 6 mass % to 8 mass % with respect to a total mass of the adhesive layer,
wherein the patch is applied to an affected part of the patient once a day,
wherein a dose of diclofenac sodium per administration is 70 mg to 150 mg, and
wherein the patch comprises liquid paraffin in the adhesive layer, and wherein the patch shows an amount of diclofenac released of 13 mg to 16 mg during a single dose and a release rate of diclofenac of 8.6% to 10.7%.

35. The method of claim 34, wherein an area of the patch is 70 cm$^2$ to 140 cm$^2$.

36. The method of claim 34, wherein a mass of an adhesive mass of the patch is 190 g/m$^2$ to 240 g/m$^2$.

37. The method of claim 34, wherein the osteoarthritis is knee osteoarthritis.

38. The method of claim 21, wherein the patch is alternately applied to inner and outer sides of a knee every day.

39. The method of claim 34, wherein the patch shows a maximum plasma concentration of diclofenac of 19 to 23 ng/mL during a single dose and a time required to reach the maximum plasma concentration of 6 to 18 hours.

40. The method of claim 34, wherein the patch shows an area under plasma drug concentration-time curve of diclofenac of 300 ng·h/mL to 400 ng·h/mL from the time of a single dose to a final time point of concentration measurement.

41. The method of claim 34, wherein the patch shows an area under plasma drug concentration-time curve of diclofenac of 300 ng·h/mL to 400 ng·h/mL when extrapolated from the time of a single dose to infinite time.

42. The method of claim 34, wherein the patch shows a half-life of the plasma concentration of diclofenac of 6 hours to 8 hours during a single dose.

43. The method of claim 34, wherein the patch shows an amount of diclofenac released of 13 mg to 16 mg during a single dose and a release rate of diclofenac of 8.6% to 10.7%.

44. The method of claim 34, wherein the patch shows a maximum plasma concentration of diclofenac of 30 ng/mL to 65 ng/mL when administration once a day is repeated to reach a steady state and a time required to reach the maximum plasma concentration of 3 to 6 hours.

45. The method of claim 34, wherein the patch shows an area under plasma drug concentration-time curve of diclofenac of 400 ng·h/mL to 700 ng·h/mL at an administration interval when administration once a day is repeated to reach a steady state.

46. The method of claim 34, wherein the patch shows a half-life of plasma concentration of diclofenac of 1 hour to 5 hours when administration once a day is repeated to reach a steady state.

47. The method of claim 34, wherein the patch shows an amount of diclofenac released of 14 mg to 21 mg when administration once a day is repeated to reach a steady state and a release rate of diclofenac of 9.3% to 14%.

48. The method of claim 34, wherein the patch comprises 3 mass % to 7 mass % of diclofenac sodium with respect to a total mass of the adhesive layer.

49. The method of claim 34, wherein the patch comprises oleic acid and citric acid as the organic acids.

50. The method of claim 49, wherein the patch comprises 4 mass % to 6 mass % of the oleic acid and 2 mass % to 4 mass % of the citric acid with respect to a total mass of the adhesive layer.

* * * * *